United States Patent [19]

Boger et al.

[11] Patent Number: 4,477,440
[45] Date of Patent: Oct. 16, 1984

[54] RENIN INHIBITORS CONTAINING AN N-TERMINAL DISULFIDE CYCLE

[75] Inventors: Joshua S. Boger, Bryn Mawr; Daniel F. Veber, Ambler, both of Pa.

[73] Assignee: Merck & Co., Inc., Rahway, N.J.

[21] Appl. No.: 531,968

[22] Filed: Sep. 14, 1983

[51] Int. Cl.³ .................... A61K 37/00; C07C 103/52
[52] U.S. Cl. .............................. 424/177; 260/112.5 R
[58] Field of Search .................. 424/177; 260/112.5 R

[56] References Cited

FOREIGN PATENT DOCUMENTS 45655  5/1981  European Pat. Off. ..... 260/112.5 R

OTHER PUBLICATIONS

Umezawa, et al., J. Antibiot. (Tokyo) 23: 259–262, 1970.
Gross et al., Science 175:656, 1971.
Tewksbury et al., Circulation 69, 60, Supp. II: 132, Oct. 1979.
Poulsen et al., Biochim. Biophys. Acta 452:533–537, 1976.
Skeggs, Jr. et al., J. Exp. Med. 106:439–453, 1957.
Kokubu et al., Biochem. Pharmacol. 22:3217–3223, 1973.
Burton et al., Biochemistry 14:3892–3898, 1975.
Poulsen et al., Biochemistry 12:3877–3882, 1973.
Haber and Burton, Fed. Proc. Fed. Am. Soc. Exp. Biol. 38:2768–2773, 1979.
Hypertension, 4, Supp. 2, 59, (1981).
Powers et al., Acid Proteases, Structure, Function and Biology, Plenum Press, 1977, 141–157.
Tang et al., Trends in Biochem. Sci., 1:205–208, 1976.
J. Biol. Chem. 251:7088–94, 1976.
Nakaie et al., Biochem. J. 205:43–47, 1982.
Marshall, Federation Proc. 35:2494–2501, 1976.
Burton et al., Proc. Natl. Acad. Sci. U.S.A. 77:5476–5479, Sep. 1980.
Suketa et al., Biochemistry 14:3188, 1975.
Swales, Pharmac. Ther. 7:173–201, 1979.
Kokubu et al., Nature 217:456–457, Feb. 3, 1968.
Matsushita et al., J. Antibiotics 28:1016–1018.
Lazar et al., Biochem. Pharma. 23:2776–2778, 1974.
Miller et al., Biochem. Pharma. 21:2941–2944, 1972.
Haber, Clinical Science 59:7s–19s, 1980.
Rich, et al., J. Org. Chem. 43:3624, 1978.
J. Med. Chem. 23:27, 1980.

Primary Examiner—Delbert R. Phillips
Attorney, Agent, or Firm—Raymond M. Speer; Hesna J. Pfeiffer

[57] ABSTRACT

Renin inhibitory peptides of the formula

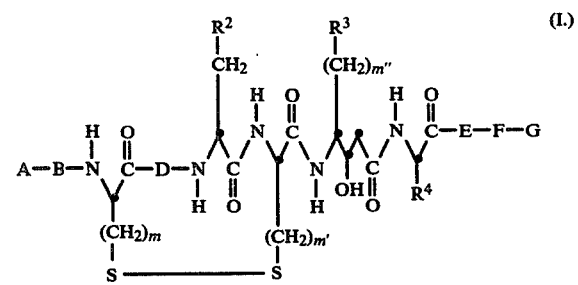

and analogs thereof inhibit renin and are useful for treating various forms of renin-associated hypertension and hyperaldosteronism.

8 Claims, No Drawings

RENIN INHIBITORS CONTAINING AN N-TERMINAL DISULFIDE CYCLE

BACKGROUND OF THE INVENTION

1. Field of The Invention

The present invention is concerned with novel peptides which inhibit renin.

The present invention is also concerned with pharmaceutical compositions containing the novel peptides of the present invention as active ingredients, with methods of treating renin-associated hypertension and hyperaldosteronism, with diagnostic methods which utilize the novel peptides of the present invention, and with methods of preparing the novel peptides of the present invention.

Renin is a proteolytic enzyme of molecular weight about 40,000, produced and secreted by the kidney. It is secreted by the juxtaglomerular cells and acts on the plasma substrate, angiotensinogen, to split off the decapeptide angiotensin I, which is converted to the potent pressor agent angiotensin II. Thus, the renin-angiotensin system plays an important role in normal cardiovascular homeostasis and in some forms of hypertension.

In the past, attempts to modulate or manipulate the renin-angiotensin system have met with success in the use of inhibitors of angiotensin I converting enzyme. In view of this success, it seems reasonable to conclude that a specific inhibitor of the limiting enzymatic step that ultimately regulates angiotensin II production, the action of renin on its substrate, would be at least equally successful. Thus, an effective inhibitor of renin has been long sought as both a therapeutic agent and as an investigative tool.

2. Brief Description of the Prior Art

There has been substantial interest in the synthesis of useful renin inhibitors for many decades; and the following table lists the major classes of renin inhibitors that have been studied, as well as their inhibition constants ($K_i$):

| Class | $K_i$ (M) |
| --- | --- |
| Renin antibody | probably $10^{-6}$ |
| Pepstatin | $10^{-6}$–$10^{-7}$ |
| Phospholipids | $10^{-3}$ |
| Substrate analogs | |
| Tetrapeptides | $10^{-3}$ |
| Octa- to tridecapeptides | $10^{-5}$–$10^{-6}$ |

Umezawa et al., in *J. Antibiot.* (Tokyo) 23: 259–262, 1970, reported the isolation of a peptide from actinomyces that was an inhibitor of aspartyl proteases such as pepsin, cathepsin D, and renin. This peptide, known as pepstatin, was found by Gross et al., *Science* 175:656, 1971, to reduce blood pressure in vivo after the injection of hog renin into nephrectomized rats. However, pepstatin has not found wide application as an experimental agent because of its limited solubility and its inhibition of a variety of other acid proteases in addition to renin. The structure of pepstatin is shown below:

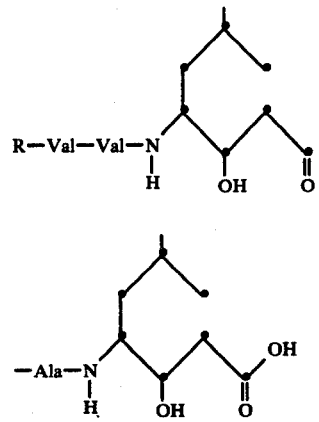

To date, many efforts have been made to prepare a specific renin inhibitor based on substrate analogy. Since the human renin substrate has only recently been elucidated (Tewksbury et al., *Circulation* 59, 60, Supp. II: 132, Oct. 1979), heretofore substrate analogy has been based on the known pig renin substrate. While the human and pig renin substrates are not the same, the substrate analogy based on pig renin has always been considered acceptable in the art as predictive of human renin inhibitory activity because of the closely related activity of the two renins. Thus, while pig renin does not cleave the human renin substrate, human renin, on the other hand, does cleave the pig renin substrate. See Poulsen et al., *Biochim. Biophys. Acta* 452:533–537, 1976; and Skeggs, Jr. et al., *J. Exp. Med.* 106:439–453, 1957. Moreover, the human renin inhibitory activity of the peptides of the present invention most active in inhibiting pig renin has been confirmed, thus providing further evidence of this accepted correlation between human and pig renin activity.

It has been found, for example, using pig renin substrate analogy, that the octapeptide sequence extending from histidine-6 through tyrosine-13 has kinetic parameters essentially the same as those of the full tetradecapeptide renin substrate. The amino acid sequence of the octapeptide in pig renin substrate is as follows:

```
  6    7    8    9   10   11   12   13
—His—Pro—Phe—His—Leu—Leu—Val—Tyr—
```

Renin cleaves this substrate between Leu[10] and Leu[11].

Kokubu et al., *Biochem. Pharmacol.* 22: 3217–3223, 1973, synthesized a number of analogs of the tetrapeptide found between residues 10 to 13, but while inhibition could be shown, inhibitory constants were only of the order of $10^{-3}$M.

Analogs of a larger segment of renin substrate were also synthesized: Burton et al., *Biochemistry* 14: 3892–3898, 1975, and Poulsen et al., *Biochemistry* 12: 3877–3882, 1973. Two of the major obstacles which had to be overcome to obtain an effective renin inhibitor useful in vivo were lack of solubility and weak binding (large inhibitory constant). Modifications to increase solubility soon established that the inhibitory properties of the peptides are markedly dependent on the hydrophobicity of various amino acid residues, and that increasing solubility by replacing lipophilic amino acids with hydrophilic isosteric residues becomes counterproductive. Other approaches to increasing solubility have had limited success. Various modifications designed to increase binding to renin have also been made, but here too, with only limited success. For a more detailed description of past efforts to prepare an effective inhibitor of renin, see Haber and Burton, *Fed. Proc. Fed. Am. Soc. Exp. Biol.* 38: 2768–2773, 1979.

More recently, Hallett, Szelke, and Jones, in work described in European Patent Publication No. 45,665 *Nature,* 299, 555 (1982), and *Hypertension,* 4, Supp. 2, 59 (1981), have replaced the Leu-Leu site of renin cleavage by isosteric substitution, and obtained compounds with excellent potency.

Powers et al., in *Acid Proteases, Structure, Function and Biology,* Plenum Press, 1977, 141–157 have suggested that in pepstatin, statine occupies the space of the two amino acids on either side of the cleavage site of a pepsin substrate, and Tang et al., in *Trends in Biochem. Sci.,* 1:205–208 (1976) and *J. Biol. Chem.,* 251:7088–94, 1976, have proposed that the statine residue of pepstatin resembles the transition state for pepsin hydrolysis of peptide bonds. However, the applicability of these concepts to renin inhibitors is not taught in any of these references, and would be speculative due to the known high degree of specificity of the renin enzyme.

Nakaie et al., *Biochem. J.* 205: 43–47, 1982, describe inhibition of renin by conformationally restricted analogs of angiotensinogen involving a disulfide bond between residues 5 and 10. However, the cyclical inhibitors of the present invention are neither described nor suggested.

For other articles describing previous efforts to devise renin inhibitors, see Marshall, *Federation Proc.* 35: 2494–2501, 1976; Burton et al., *Proc. Natl. Acad. Sci. USA* 77: 5476–5479, Sept. 1980; Suketa et al., *Biochemistry* 14: 3188, 1975; Swales, *Pharmac. Ther.* 7: 173–201, 1979; Kokubu et al., *Nature* 217: 456–457, Feb. 3, 1968; Matsushita et al., *J. Antibiotics* 28: 1016–1018, Dec. 1975; Lazar et al., *Biochem. Pharma.* 23: 2776–2778, 1974; Miller et al., *Biochem. Pharma.* 21: 2941–2944, 1972; Haber, *Clinical Science* 59:7s–19s, 1980; and Rich et al., *J. Org. Chem.* 43: 3624, 1978, and *J. Med. Chem.* 23: 27, 1980.

DETAILED DESCRIPTION OF THE INVENTION AND PREFERRED EMBODIMENTS

In accordance with the present invention there are provided renin inhibitory peptides of the formula:

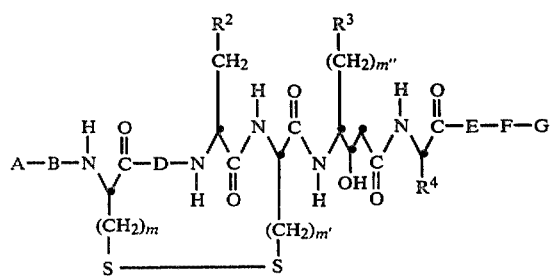

wherein:

A is hydrogen; or

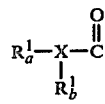

where X is

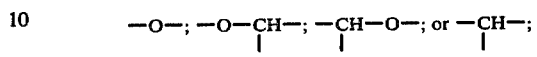

and $R_a^1$ and $R_b^1$ may be the same or different and are hydrogen; Y—(CH$_2$)$_n$— where Y is C$_{1-4}$alkyl; hydrogen; aryl; C$_{3-7}$cycloalkyl; or C$_{3-7}$cycloalkyl or aryl substituted with up to five members independently selected from the group consisting of C$_{1-8}$alkyl, trifluoromethyl, hydroxy, C$_{1-4}$alkoxy, and halo; n is 0 to 5; except that where X is —O—, only one of $R_a^1$ or $R_b^1$ is present;

B is absent; glycyl; sarcosyl; or

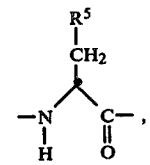

where $R^5$ is hydrogen; C$_{1-4}$ alkyl; hydroxy C$_{1-4}$ alkyl; aryl; aryl substituted with up to three members selected from the group consisting of C$_{1-4}$alkyl, trifluoromethyl, hydroxy, C$_{1-4}$alkoxy, and; halo; indolyl; 4-imidazolyl; amino C$_{2-4}$ alkyl; guanidyl C$_{2-3}$ alkyl; or methylthiomethyl;

D is

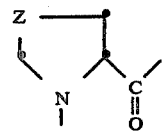

where Z is —(CH$_2$)$_p$— and p is 1 or 2; or —S—;

E is absent; or

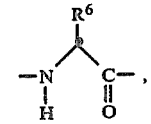

where $R^6$ is hydrogen;

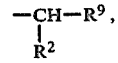

where $R^9$ is hydrogen, C$_{1-4}$alkyl, hydroxy, or C$_{3-7}$cycloalkyl; or —CH$_2$R$^{10}$, where R$^{10}$ is 4-imidazolyl, amino-C$_{2-4}$alkyl, 2-, 3- or 4-pyridyl, or guanidyl-C$_{2-3}$alkyl;

F is absent; glycyl; sarcosyl; or

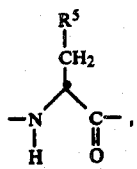

where $R^5$ is as defined above;

G is OR; NHR; N(R)₂, where each R may be the same or different and is hydrogen; or $C_{1-4}$alkyl; or, when E and/or F are absent, G may be (1) —Y—(CH₂)$_q$—$R^7$ where Y is —NH— or —O—; q is 0 to 5; and $R^7$ is hydrogen; hydroxy; $C_{1-4}$alkyl; $C_{3-7}$cycloalkyl; aryl; aryl substituted with up to five members independently selected from the group consisting of $C_{1-6}$alkyl, trifluoromethyl, hydroxy, $C_{1-4}$alkoxy, amino, mono- or di$C_{1-4}$alkylamino, and halo; amino; mono-, di- or tri-$C_{1-4}$alkylamino; guanidyl; heterocyclic; or heterocyclic substituted with up to five members independently selected from the group consisting of $C_{1-6}$alkyl, hydroxy, trifluoromethyl, $C_{1-4}$alkoxy, halo, aryl, aryl-$C_{1-4}$alkyl, amino, and mono- or di-$C_{1-4}$alkylamino;

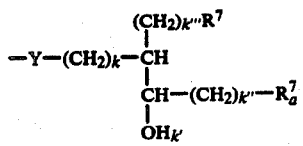
(2)

where Y is as defined above; k is 0 or 1; k' is 0 or 1 k" is 1 to 4 k'" is 1 to 4; and $R^7$ and $R_a{}^7$ may be the same or different and have the same meaning as $R^7$ above and $R_a{}^7$ may additionally be

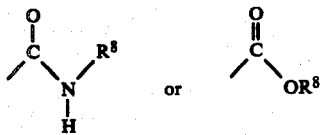

where $R^8$ is hydrogen or $C_{1-3}$alkyl; or

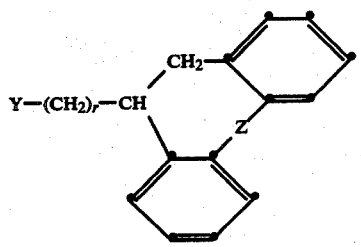
(3)

where Y is as defined above; r is 0 or 1; and Z is

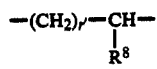
(a)

where r' is 0 or 1; and $R^8$ is as defined above; or

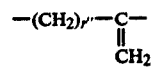
(b)

where r" is 0 or 1;

$R^2$ is hydrogen; $C_{1-4}$alkyl; aryl; aryl substituted with up to three members selected from the group consisting of $C_{1-4}$alkyl, trifluoromethyl, hydroxy, $C_{1-4}$alkoxy, and halo; or indolyl;

$R^3$ is $C_{3-6}$ alkyl; $C_{3-7}$ cycloalkyl; aryl; or $C_{3-7}$cycloalkyl or aryl substituted with up to three members selected from the group consisting of $C_{1-4}$alkyl, trifluoromethyl, hydroxy, $C_{1-4}$alkoxy, and halo;

$R^4$ is hydrogen; or

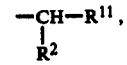

where $R^{11}$ is hydrogen; $C_{1-4}$alkyl; hydroxy; or $C_{3-7}$cycloalkyl; and $R^2$ is as defined above; and m is 1 or 2;
m' is 1 or 2;
m" is 1 to 4; and wherein all of the asymmetric carbon atoms have an S configuration, except for those in the A, B, D, F, and G substituents; which may have an S or R configuration; and a pharmaceutically acceptable salt thereof.

While both the S and R chiralities for asymmetric carbon atoms in the A, B, D, F, and G substituents are included in the peptides of the present invention, preferred chiralities are indicated in the description which follows.

In the above definitions, the term "alkyl" is intended to include both branched and straight chain hydrocarbon groups having the indicated number of carbon atoms.

The term "halo" means fluoro, chloro, bromo and iodo.

The aryl substituent represents phenyl, and naphthyl.

The heterocyclic substituent recited above represents any 5- or 6-membered aromatic ring containing from one to three heteroatoms selected from the group consisting of nitrogen, oxygen, and sulfur; having various degrees of saturation; and including any bicyclic group in which any of the above heterocyclic rings is fused to a benzene ring. Heterocyclic substituents in which nitrogen is the heteroatom are preferred, and of these, those containing a single nitrogen atom are preferred. Fully saturated heterocyclic substituents are also preferred. Thus, piperidine is a preferred heterocyclic substituent. Other preferred heterocyclic substituents are: pyrryl, pyrrolinyl, pyrrolidinyl, pyrazolyl, pyrazolinyl, pyrazolidinyl, imidazolyl, imidazolinyl, imidazolidinyl, pyridyl, piperidinyl, pyrazinyl, piperazinyl, pyrimidinyl, pyridazinyl, oxazolyl, oxazolidinyl, isoxazolyl, isoxazolidinyl, morpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl and benzothienyl.

Where the heterocyclic substituent itself is substituted, it is preferred that the substituent be aryl$C_{1-4}$alkyl.

The novel renin inhibitory peptides of the present invention may also be described in terms of common amino acid components and closely related analogs thereof, in accordance with the following formula:

  (II.)

The A, B, D, E, F, and G components correspond to the same portions of Formula I.

In Formula II, Sta represents the unusual amino acid statine and its closely related analogs, and its presence constitutes a unique feature of the renin inhibitory peptides of the present invention. Statine may be named as 4(S)-amino-3(S)-hydroxy-6-methylheptanoic acid, and may be represented by the following formula:

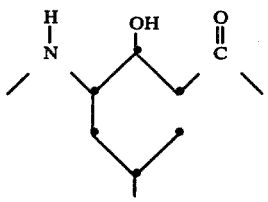  (III)

As shown in Formula III above, the delta-substituent in naturally-occurring statine is isopropyl, or a leucine sidechain, essentially. As shown in Formula I by the $R^3$ substituents, the isopropyl group may be replaced by higher alkyl groups up to six carbon atoms, cycloalkyl groups containing from three to seven carbon atoms, aryl, and $C_{3-7}$cycloalkyl or aryl substituted with up to three members selected from the group consisting of $C_{1-4}$alkyl, trifluoromethyl, hydroxy, $C_{1-4}$alkoxy, fluoro, chloro, bromo, and iodo. A phenyl substituent and a cyclohexyl substituent are especially preferred. These modifications of the naturally-occurring statine structure are in accordance with the hydrophobicity considered necessary to maintain the inhibitory activity of the total peptide.

The remaining common amino acid components of Formula II are as follows:

A has the same meaning as above in Formula I;
B is Gly, Sar, Ala, Leu, Ser, Thr, Phe, Tyr, Trp, His, Lys, Orn, Arg, or Met;
C is Cys or Hcys: one end of the disulfide cyclical structure;
D is Pro;
H is Ala, Leu, Phe, Tyr, or Trp;
I is Cys or Hcys: the other end of the cyclical structure;
J is Gly, Ala, Val, Leu, Ile, Ser, Thr, Phe, Tyr, or Trp;
E is the same as J and may also be Lys, Orn, Arg, or His;
F is the same as B; and
G has the same meaning as above in Formula I.

It will be understood that closely related analogs of the above common amino acids, for example, aliphatic amino acids in addition to Ala, Val, Leu, and Ile, such as α-aminobutyric acid (Abu), and substituted phenyl derivatives of Phe, are included in the broad description of the novel inhibitory peptides of the present invention represented by Formula I and its definitions. Thus, the peptides of Formula II and its definitions, including the derivatives of naturally-occurring statine represented by the definitions of the $R^3$ substituent in Formula I, represent preferred peptides of the present invention.

Preferred inhibitory peptides of the present invention are the following:

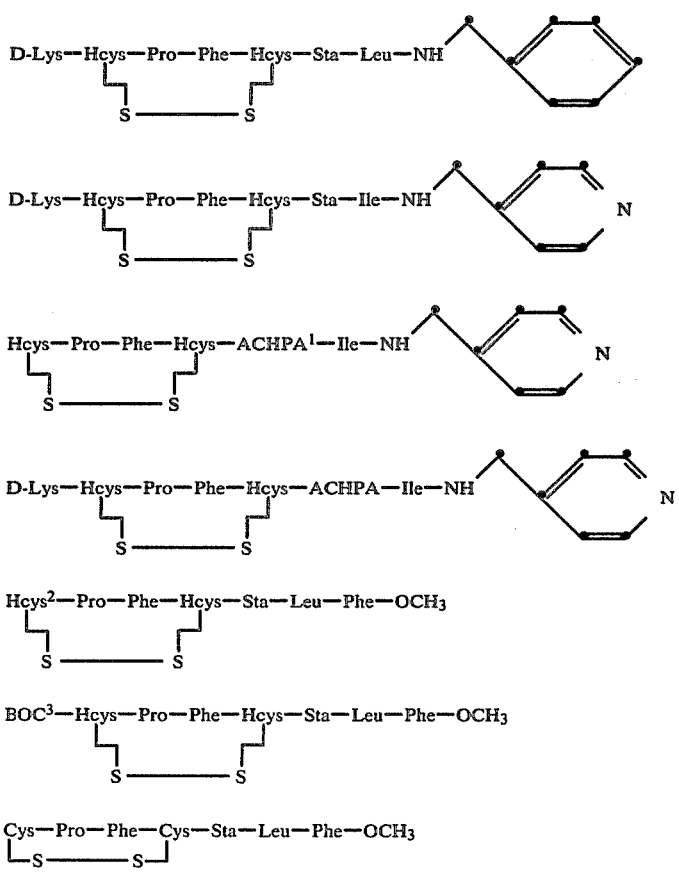

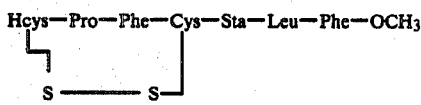

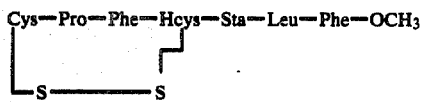

[1]ACHPA = (3S,4S)-4-amino-5-cylcohexyl-3-hydroxypentanoic acid
[2]Hcys = L-homocysteine
[3]BOC = Tert-butyloxycarbonyl The inhibitory peptides of the present invention may be better appreciated in terms of substrate analogy from the following illustration of Formula I alongside the octapeptide sequence of a portion of the pig renin substrate, which renin cleaves between Leu[10] and Leu[11]:

Pro Phe His Leu Leu Val Tyr
7    8   9   10  (11) 12  13  (14)

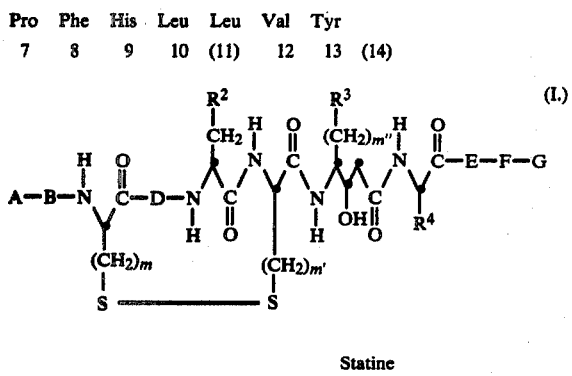

Statine

As can be seen, a unique aspect and essential feature of the present invention is the substitution of the single statine amino acid component for the double amino acid sequence: Leu[10]-Leu[11] in the endogenous pig renin substrate. It is believed that substitution of statine for both leucine amino acids rather than just one leucine results in an improved substrate analogy due to the greater linear extent of statine as compared to a single leucine component. Thus, statine more closely approximates Leu-Leu in linear extent, and thereby provides a better "fit" to the renin enzyme.

The inhibitory peptides of the present invention may also be better appreciated in terms of substrate analogy from the following illustration of Formula I alongside the octapeptide sequence of a portion of the human renin substrate, which renin cleaves between Leu[10] and Val[11]:

Pro Phe His Leu Val Ile His
7    8   9   10  (11) 12  13  (14)

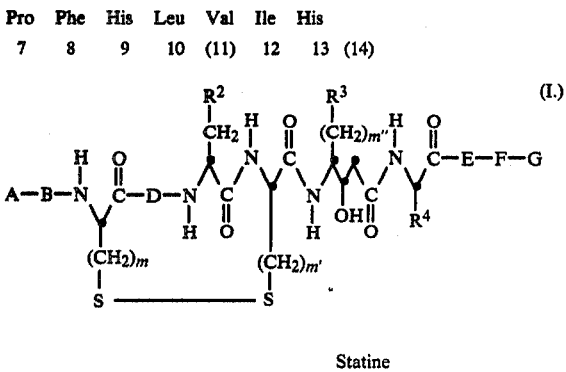

Statine

As can be seen, a unique aspect and essential feature of the present invention is the substitution of the single statine amino acid component for the double amino acid sequence: Leu[10]-Val[11] in the endogenous human renin substrate. It is believed that substitution of statine for both the leucine and valine amino acids rather than just the leucine results in an improved substrate analogy due to the greater linear extent of statine as compared to a single leucine component. Thus, statine more closely approximates Leu-Val in linear extent, and thereby provides a better "fit" to the human renin enzyme.

In the endogenous substrate it is also preferred to substitute Leu for Val[12] and Phe for Tyr[13] in order to enhance the inhibitory activity of the resulting peptide.

The Formula I compounds can be used in the form of salts derived from inorganic or organic acids and bases. Included among such acid addition salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups can be quaternized with such agents as lower alkyl halides, such as methyl, ethyl, propyl, and butyl chloride, bromides and iodides: dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

The novel peptides of the present invention possess an excellent degree of activity in treating renin-associated hypertension and hyperaldosteronism.

For these purposes the compounds of the present invention may be administered parenterally, by inhalation spray, or rectally in dosage unit formulations containing conventional non-toxic pharmaceutically acceptable carriers, adjuvants and vehicles. The term parenteral as used herein includes subcutaneous injections, intravenous, intramuscular, intrasternal injection of infusion techniques. In addition to the treatment of warm-blooded animals such as mice, rats, horses, dogs, cats, etc., the compounds of the invention are effective in the treatment of humans.

The pharmaceutical compositions may be in the form of a sterile injectable preparation, for example as a sterile injectable aqueous or oleagenous suspension. This suspension may be formulated according to the known art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectibles.

The peptides of this invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Dosage levels of the order of 2 to 35 grams per day are useful in the treatment of the above indicated conditions. For example, renin-associated hypertension and hyperaldosteronism are effectively treated by the administration of from 30 milligrams to 0.5 grams of the compound per kilogram of body weight per day.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

Thus, in accordance with the present invention there is further provided a pharmaceutical composition for treating renin-associated hypertension and hyperaldosteronism, comprising a pharmaceutical carrier and a therapeutically effective amount of a peptide of the formula:

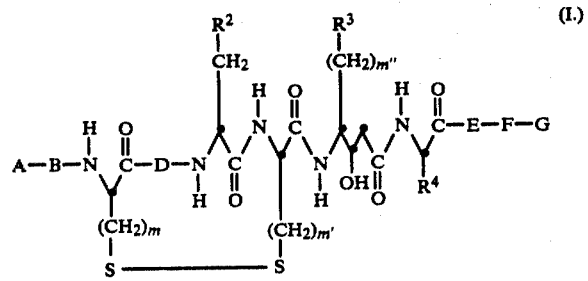

wherein A, B, D, $R^2$, $R^3$, $R^4$, E, F, and G have the same meaning as recited further above for Formula I; wherein all of the asymmetric carbon atoms have an S configuration, except for those in the A, B, D, F, and G substituents, which may have an S or R configuration; and a pharmaceutically acceptable salt thereof.

Also, in accordance with the present invention there is still further provided a method of treating renin-associated hypertension and hyperaldosteronism, comprising administering to a patient in need of such treatment, a therapeutically effective amount of a peptide of the formula:

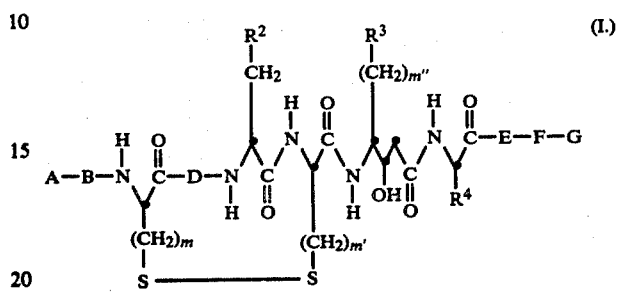

wherein A, B, D, $R^2$, $R^3$, $R^4$, E, F, and G have the same meaning as recited further above for Formula I; wherein all of the asymmetric carbon atoms have an S configuration, except for those in the A, B, D, F, and G substituents, which may have an S or R configuration; and a pharmaceutically acceptable salt thereof.

The renin inhibitory novel peptides of the present invention may also be utilized in diagnostic methods for the purpose of establishing the significance of renin as a causative or contributory factor in hypertension or hyperaldosteronism in a particular patient. For this purpose the novel peptides of the present invention may be administered in a single dose of from 0.1 to 10 mg per kg of body weight.

Both in vivo and in vitro methods may be employed. In the in vivo method, a novel peptide of the present invention is administered to a patient, preferably by intravenous injection, although parenteral administration is also suitable, at a hypotensive dosage level and as a single dose, and there may result a transitory fall in blood pressure. This fall in blood pressure, if it occurs, indicates supranormal plasma renin levels.

An in vitro method which may be employed involves incubating a body fluid, preferably plasma, with a novel peptide of the present invention and, after deproteinization, measuring the amount of angiotensin II produced in nephrectomized, pentolinium-treated rats. Another in vitro method involves mixing the plasma or other body fluid with a novel peptide of the present invention and injecting the mixture into a test animal. The difference in pressor response with and without added peptide is a measure of the renin content of the plasma.

Pepstatin may be employed in the methods described above as an active control. See, e.g., U.S. Pat. Nos. 3,784,686 and 3,873,681 for a description of the use of pepstatin in diagnostic methods of this type.

The novel peptides of the present invention may be prepared in accordance with well-known procedures for preparing peptides from their constituent amino acids, which will be described in more detail below. The unusual amino acid, statine, may be prepared in accordance with the procedure described by Rich et. al., *J. Org. Chem.* 43: 3624 (1978).

A general method of preparation may be described in the following terms; wherein amino acids forming peptides of various lengths are sequentially assigned a Roman numeral for each peptide, rather than on the basis of a position in the overall peptide Formula I:

A method of preparing a peptide of Formula I, said peptide being comprised of from six to nine amino acids identified as I through IX, amino acid (AA) I being at the C-terminus of said peptide to which substituent G is attached, and amino acid (AA) VI through IX, depending upon the number of amino acids present, being at the N-terminus of said peptide, to which substituent A is attached, said peptide of Formula I being cyclical by virtue of a disulfide bond between AA III, IV, or V, and AA VI, VII, or VIII, respectively, comprising the steps of:

(A) treating an ester of the C-terminus amino acid (AA I) with the next adjacent amino acid (AA II) of said peptide, the amino group of said amino acid being protected by a protecting group, in the presence of a condensing agent, whereby a dipeptide of the two amino acids (AA I and II) is formed;

(B) deprotecting the dipeptide formed in Step (A) by removing the protecting group from the amino group of AA II;

(C) repeating the procedures of Steps A and B successively to form a hexapeptide to an octapeptide of AA's I-II-III-IV-V-VI or VII, or VIII, without, however, removing the protecting group from the amino group of AA VI, VII, or VIII; and providing a protecting group on the sulfur atoms of AA's III, IV, or V and VI, VII, or VIII, respectively;

(D) forming the methyl ester of AA I, if said ester is not employed initially;

(E) cyclizing the hexapeptide to octapeptide by forming a disulfide bond between AA III, IV, or V, and AA VI, VII, or VIII, respectively, through deprotection of the sulfur atoms followed by oxidative coupling; to give the peptide of Formula I wherein A is hydrogen;

(F) removing the protecting group from the amino group of AA VI, VII, or VIII;

(G) treating the cyclical hexapeptide to octapeptide formed in Step (E) with

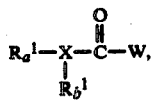

where X, $R_a^1$, and $R_b^1$, are as defined above and W is an acid halide, anhydride, or other carbonyl activating group, to give the peptide of Formula I wherein A is other than hydrogen;

(H) where a cyclical hexapeptide is formed, treating it with hydrazine to give the corresponding hydrazide, followed by treatment of said hydrazide with acidic nitrite to give the corresponding acyl azide, followed by treatment of said acyl azide with the appropriate amine compound to give the desired G substituent in the peptide of Formula I when E and/or F are absent; said method also comprising, where necessary, protection of sidechain substituents of the component amino acids AA I through AA IX, with deprotection being carried out as a final step; said method also comprising any combination of the steps set out above, whereby the amino acids I through IX and substituents A and G are assembled in any desired order to prepare the peptide of Formula I; said method also comprising employment of the steps set out above in a solid phase sequential synthesis, whereby in the initial step the carboxyl group of the selected amino acid is bound to a synthetic resin substrate while the amino group of said amino acid is protected, followed by removal of the protecting group, the succeeding steps being as set out above, the peptide as it is assembled being attached to said synthetic resin substrate; followed by a step of removing the peptide from said synthetic resin substrate by transesterification with methanol to give the methyl ester of AA I, followed by hydrolysis and cyclization as recited above; removal of sidechain protecting groups being accomplished either before or after removal of the peptide from said synthetic resin substrate; the steps of cyclization and formation of the A and G substituents in said method being accomplished at any time and in any order during preparation of peptides of different linear extent.

A preferred method involves preparation of the peptide of desired linear extent and desired A substituent by solid phase sequential synthesis, which is then removed by transesterification to give the linear, protected (N-terminus) methyl ester in which the sulfur atoms to form the disulfide bond are also blocked. Cyclization is effected using excess iodine in dimethylformamide or dimethylformamide in water, quenching after 15–30 minutes with excess zinc dust, and filtering to give the desired cyclized peptide. The N-terminus protecting group, preferably t-butyloxycarbonyl, is removed with trifluoroacetic acid, hydrochloric acid in ethyl acetate, or liquid hydrofluoric acid with 10% anisole, to give the free amino compound, as its salt. In the step of deprotection, 1% ethanedithiol is added to reduce side reactions involving sulfur.

Where the C-terminus is to be a non-amino acid ending, i.e., where E and F are absent, then the G substituent is added at an intermediate stage. For example,

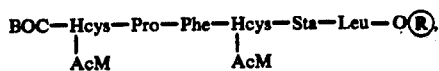

where Ⓡ represents the resin substrate used in the solid phase sequential synthesis, is prepared on the resin, removed by methanolysis-(transesterification), and hydrolyzed to give the free . . . LeuOH. This material is then condensed using, e.g., diphenylphosphoryl azide, with the appropriate amine to give the desired G substituent:

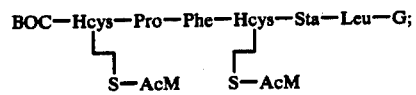

and the synthesis is then completed, including cyclization, as has already been described above.

The phenyl analog of statine, (3S,4S)-4-amino-3-hydroxy-5-phenylpentanoic acid (AHPPA) can be prepared in accordance with the procedure described by Rich et al., *J. Med. Chem.* 23: 27–33 (1980).

Other analogs of statine may be prepared in a straightforward manner. For example, the cyclohexylalanine analog of statine, (3S,4S)-4-amino-5-cyclohexyl-3-hydroxypentanoic acid (ACHPA) can be prepared by catalytic hydrogenation (using $H_2Rh$ on alumina, or other suitable catalyst) of the BOC-AHPPA, prepared as described in the paragraph immediately above. Alternatively, this and similar statine analogs can be prepared in accordance with the procedure described for statine, where the BOC-Leu starting material is replaced with the amino acid containing the desired side chain. Thus, BOC-ACHPA can also be prepared starting from BOC-L-cyclohexylalanine, itself prepared, for example, by catalytic reduction of BOC-Phe, in the same manner as described for BOC-AHPPA.

The novel inhibitory peptides of the present invention are prepared by using the solid phase sequential synthesis technique.

In the following description several abbreviated designations are used for the amino acid components, certain preferred protecting groups, reagents and solvents. The meanings of such abbreviated designations are given below in Table I.

| Abbreviated Designation | |
|---|---|
| | Protecting Groups |
| ACM | acetamidomethyl |
| BOC | tert-butyloxycarbonyl |
| CBZ | benzyloxycarbonyl |
| 2-Cl—CBZ | 2-chlorobenzyloxycarbonyl |
| IBU | iso-butyryl |
| IVA | iso-valeryl |
| DNP | dinitrophenyl |
| OMe | methyl ester |
| | Activating Groups |
| HBT | 1-hydroxybenzotriazole |
| | Condensing Agents |
| DCCI | dicyclohexylcarbodiimide |
| DPPA | diphenylphosphorylazide |
| | Reagents |
| TEA | triethylamine |
| TFA | trifluoroacetic acid |
| | Solvents |
| A | ammonium hydroxide (conc.) |
| AcOH | acetic acid |
| C | chloroform |
| DMF | dimethylformamide |
| E | ethyl acetate |
| M | methanol |
| P | pyridine |
| THF | tetrahydrofuran |
| W | water |

The synthesis of the peptides of the present invention by the solid phase technique is conducted in a stepwise manner on chloromethylated resin. The resin is composed of fine beads (20–70 microns in diameter) of a synthetic resin prepared by copolymerization of styrene with 1–2 percent divinylbenzene. The benzene rings in the resin are chloromethylated in a Friedel-Crafts reaction with chloromethyl methyl ether and stannic chloride. The Friedel-Crafts reaction is continued until the resin contains 0.5 to 5 mmoles of chlorine per gram of resin.

The amino acid selected to be the C-terminal amino acid of the linear peptide is converted to its amino protected derivative. The carboxyl group of the selected C-terminal amino acid is bound covalently to the insoluble polymeric resin support, as for example, as the carboxylic ester of the resin-bonded benzyl chloride present in chloromethyl-substituted polystyrene-divinylbenzene resin. After the amino protecting group is removed, the amino protected derivative of the next amino acid in the sequence is added along with a coupling agent, such as dicyclohexylcarbodiimide. The amino acid reactant may be employed in the form of a carboxyl-activated amino acid such as ONP ester, an amino acid azide, and the like. Deprotection and addition of successive amino acids is performed until the desired linear peptide is formed.

The selection of protecting groups is, in part, dictated by particular coupling conditions, in part by the amino acid and peptide components involved in the reaction.

Amino-protecting groups ordinarily employed include those which are well known in the art, for example, urethane protecting substituents such as benzyloxycarbonyl (carbobenzoxy), p-methoxycarbobenzoxy, p-nitrocarbobenzoxy, t-butyoxycarbonyl, and the like. It is preferred to utilize t-butyloxycarbonyl (BOC) for protecting the α-amino group in the amino acids undergoing reaction at the carboxyl end of said amino acid. The BOC protecting group is readily removed following such coupling reaction and prior to the subsequent step by the relatively mild action of acids (i.e. trifluoroacetic acid, or hydrogen chloride in ethyl acetate).

The OH group of Thr and Ser can be protected by the Bzl group and the -amino group of Lys can be protected by the INOC group or the 2-chlorobenzyloxycarbonyl (2-Cl-CBZ) group. Neither group is affected by TFA, used for removing BOC protecting groups. After the peptide is formed, the protective groups, such as 2-Cl-CBZ and Bzl, can be removed by treatment with HF or by catalytic hydrogenation.

The thiol group of Cys and Hcys can be protected with the acetamidomethyl (ACM) group, preferred as described in the examples, or by other well-known protecting groups, such as benzyl. The ACM group is best removed during cyclization with iodine, although it can be removed before cyclization with mercury, followed by iodine or air oxidation for cyclization.

After the peptide has been formed on the solid phase resin, it may be removed from the resin by a variety of methods which are well known in the art. For example the peptide may be cleaved from the resin with hydrazine, by ammonia in methanol, or by methanol plus a suitable base.

Preparation of the novel inhibitory peptides of the present invention utilizing the solid phase technique is illustrated in the following examples, which however, are not intended to be any limitation of the present invention.

EXAMPLE 1

N<sup>α</sup>-butyloxycarbonyl-S-(acetamidomethyl)-L-homocysteine

This blocked amino acid derivative used in the subsequent syntheses was prepared according to modifications of literature procedures.

L-S-benzylhomocysteine was prepared according to the method of C. A. Dekker and J. S. Fruton, *J. Biol. Chem.* 173 471 (1948), starting from L-methionine in 27% overall yield. The S-benzyl group was removed following the procedures of V. du Vigneaud and W. I. Patterson, J. Biol. Chem. 109 97 (1935), and of H. Dyer, J. Biol. Chem. 124 519 (1938), giving free L-homocysteine. Protection of the free thiol group as the S-acetamido methyl was accomplished following the procedures described by P. Marbach and J. Rudinger, *Helv. Chim. Acta.* 57 403 (1974) for similar protection of cysteine. This procedure, using acetamidomethanol and hydrofluoric acid at low temperature gave a crude product containing predominantly the desired S-acetamidomethyl-L-homocysteine. This mixture was reacted with di-tert-butyl-dicarbonate (BOC$_2$O) in DMF containing diisopropylethylamine to give after workup the title crude protected amino acid. The product ($R_f$=0.44, TLC 80:20:1:2; chloroform:methanol:a- cetic acid:water) is contaminated with some side product at $R_f=0.63$. This side product can be easily removed by silica gel chromatography giving the pure BOC-(ACM)-L-homocysteine.

EXAMPLE 2

N—tert-butyloxycarbonyl-L-

Homocysteinyl-L-Prolyl-L-Phenylalanyl-L-Homocysteinyl-
|_____|

(3S,4S)—Statyl-L-Leucyl-L-Phenylalanine methyl ester

The title peptide, where the bracket beneath the name indicates the points of cyclization from L-Homocysteine to L-Homocysteine by a disulfide link, was prepared by a combination of solid phase and solution methods.

Step A:
BOC-L-Homocys(ACM)-L-Pro-L-Phe-L-Homocys-(ACM)-(3S,4S)-Sta-L-Leu-L-Phe-O-Resin The title peptide resin was prepared by standard solid phase methodology as described in Erickson and Merrifield, *Proteins*, 3rd ed., 2, 257–527 (1971), using a Beckman 990B peptide synthesizer to carry out the operations according to the attached programs. The starting polymer was BOCPhe esterified to 2% cross-linked polystyrenedivinylbenzene (2 mmole, 1.7 g). The N-BOC derivatives of L-Homocys(ACM), Pro, Phe, and Leu were coupled using DCCI with an equivalent of the additive 1-hydroxybenzotriazole. The L-Homocysteine derivative was prepared as described in Example 1. The Sta derivative (BOC) was prepared in accordance with Rich, et al. *J. Org. Chem.* 43 3624 (1978). The BOC group was removed with 40% TFA. In all BOC-removal steps following the introduction of Homocys (or Cys in other examples), 1% ethanedithiol was added to the 40% TFA solution in dichloromethane ($CH_2Cl_2$) as a scavenger to protect the sulfur atom from side reactions during the BOC-removal. A coupling of 30 minutes followed by a recoupling of 60 minutes (2.5 equivalents each time of BOC-amino acid in 1:1 $CH_2Cl_2$/DMF with DCCI and $HBT.H_2O$) were used for each amino acid except Sta and Hcys. In order to conserve supplies of these two rarer amino acids, an initial coupling of 1.25 equivalents of BOC-amino acid with DCCI and $HBT.H_2O$ in 1.25 equivalent amounts for 18 hours was followed by Steps 1-3 of the recouple program 2 and an additional coupling of 18 hours using the original (saved) coupling solution. This effected >99% complete reaction, preserving their supply.

Step B:
BOC-L-Homocys(ACM)-Pro-Phe-L-Homocys-(ACM)-Sta-Leu-Phe-OCH₃

The completed resin from Step A above, approximately 3.5 g, was suspended in 50 ml dry methanol (MeOH) under $N_2$, to which 5 ml diisopropylethylamine (DIPEA) was added. The suspension was stirred for 40 hours, filtered, and the resin washed with $CH_2Cl_2$ and MeOH. The combined filtrates were evaporated to give 3.3 g of a crude white residue. This proved to be predominantly a single compound by TLC, 80:20:2:1 chloroform:methanol:water:acetic acid, $R_f=0.63$. Amino acid analysis revealed the expected amino acid ratios.

Step C:
BOC—Hcys—Pro—Phe—Hcys—Sta—Leu—Phe—OCH₃
|_____|

The linear material from Step B above was cyclized by dissolving a 1.56 g portion in 1000 ml 80:20, $DMF:H_2O$. To this was added a solution of 3.38 g iodine in 250 ml 80:20, $DMF:H_2O$. This mixture was stirred for 5 hours and the reaction quenched by addition of 7 g zinc dust, adding rapidly in portions until the solution became colorless. The solution was filtered and evaporated to give a yellow oil. This oil was dissolved in 400 ml ethylacetate and washed repeatedly with water. The organic layer was dried over $Na_2SO_4$ and concentrated to dryness to give 1.08 g of an orange residue. Thin layer chromatography in 90:10:0.5 chloroform:methanol:water showed predominantly one spot at $R_f=0.42$ and none of the starting material B at $R_f=0.32$. Purification on silica chromatography gave 0.400 g of a pure product by TLC, along with 0.480 g of slightly impure side cuts. The pure fractions were combined, evaporated and precipitated from $CH_2Cl_2$/heptane to give a white powder. HPLC: 98.2%. Spinco: Pro₁.₀₄ Phe₀.₉₆ Leu₁.₀₄ Phe₀.₉₆, Sta and Hycs not analyzed, 96% peptide content. 360 MHz, ¹H NMR and 90 MHz¹³CNMR consistent with structure.

Elemental analysis: Calc for $C_{51}H_{75}N_7O_{11}S_2.H_2O$ (FW=1044.3):

|  | C | H | N | S |
|---|---|---|---|---|
| Calc: | 58.66 | 7.43 | 9.39 | 6.14 |
| Found: | 58.87 | 7.57 | 9.08 | 4.41 |

The FAB (fast atom bombardment) mass spectrogram shows parent ion for monomeric cyclic structure MW 1026.3.

EXAMPLE 3

L-Homocysteinyl-L-Prolyl-L-Phenylalanyl-L-Homocysteinyl-
|_____|

(3S,4S)—Statyl-L-Leucyl-L-Phenylalanine methyl ester, trifluoroacetic acid salt

The title peptide was prepared by removal of the BOC group from the material prepared in Example 2.

To 50.0 mg of BOC-Hcys-Pro-Phe-Hcys-Sta-Leu-Phe-OCH₃ (see Example 2 above) was added 4 ml of a solution of 1% ethanedithiol in trifluoroacetic acid. The solution was kept under $N_2$ for 2½ hours and evaporated to a film. The residue was triturated with ether and the solid filtered and dried to give 43.3 mg of the title product. TLC, 80:20:2, chloroform:methanol:water, $R_f=0.18$ (versus $R_f=0.38$ for starting material). HPLC: 98.9% pure. 360 MHz ¹H NMR consistent with structure. Spinco: Hcys Pro₀.₉₉ Phe₁.₀₀ Hcys Sta Leu₁.₀₂ Phe₁.₀₀; 82% peptide content based upon MW=925.7. Elemental analysis: Calc for TFA.3H₂O, FW=1093.8, $C_{46}H_{67}N_7O_9S_2.C_2HF_3O_2.3(H_2O)$

|  | C | H | N |
|---|---|---|---|
| Calc: | 52.74 | 6.82 | 8.97 |

-continued

|  | C | H | N |
|---|---|---|---|
| Found: | 52.50 | 6.34 | 8.73 |

SCHEDULE OF STEPS FOR 2 MMOL RUN

| Step | Solvent/Reagent | Vol. (ml) | Mix time (min) |
|---|---|---|---|
| Coupling Program 1 | | | |
| 1 | CH$_2$Cl$_2$ | 6 × 20 | 2 |
| 2 | 40% TFA in CH$_2$Cl$_2$ | 1 × 20 | 2 |
| 3 | 40% TFA in CH$_2$Cl$_2$ | 1 × 20 | 25 |
| 4 | CH$_2$Cl$_2$ | 3 × 20 | 2 |
| 5 | 10% TEA in CH$_2$Cl$_2$ | 2 × 20 | 5 |
| 6 | CH$_2$Cl$_2$ | 3 × 20 | 2 |
| 7 | BOC-amino acid, HBT in 1:1 DMF/CH$_2$Cl$_2$ | 20 | 5 |
| 8 | 1.0M DCCI in CH$_2$Cl$_2$ | 5 | 30 |
| 9 | DMF | 1 × 20 | 2 |
| 10 | MeOH | 2 × 20 | 2 |
| 11 | CH$_2$Cl$_2$ | 1 × 20 | 2 |
| Re-Couple Program 2 | | | |
| 1 | CH$_2$Cl$_2$ | 1 × 20 | 2 |
| 2 | 10% TEA in CH$_2$Cl$_2$ | 2 × 20 | 5 |
| 3 | CH$_2$Cl$_2$ | 3 × 20 | 2 |
| 4 | BOC-amino acid, HBT in 1:1 DMF/CH$_2$Cl$_2$ | 20 | 5 |
| 5 | 1.0M DCCI in CH$_2$Cl$_2$ | 15 | 60 |
| 6 | DMF | 1 × 20 | 2 |
| 7 | MeOH | 2 × 20 | 2 |
| 8 | CH$_2$Cl$_2$ | 5 × 20 | 2 |
| Program 3 (DNP removal) | | | |
| 1 | CH$_2$Cl$_2$ | 1 × 20 | 2 |
| 2 | DMF | 2 × 20 | 2 |
| 3 | 10% phenylthiol in DMF | 1 × 20 | 25 |
| 4 | DMF | 1 × 20 | 2 |
| 5 | 10% TEA in CH$_2$Cl$_2$ | 1 × 20 | 2 |
| 6 | DMF | 2 × 20 | 2 |
| 7 | 10% phenylthiol in DMF | 1 × 20 | 25 |
| 8 | DMF | 3 × 20 | 2 |
| 9 | MeOH | 2 × 20 | 2 |
| 10 | CH$_2$Cl$_2$ | 2 × 20 | 2 |
| 11 | MeOH | 2 × 20 | 2 |
| 12 | CH$_2$Cl$_2$ | 2 × 20 | 2 |
| 13 | MeOH | 2 × 20 | 2 |

EXAMPLE 4–6

Following the standard solid phase methodology described above in Example 2, additional inhibitory peptides of the present invention were prepared. The peptides prepared are set out in the following table. Satisfactory amino acid analyses were obtained by Spinco method for each listed peptide.

| Exm. No. | Peptide |
|---|---|
| 4. | Cys—Pro—Phe—Cys—Sta—Leu—Phe—OCH$_3$ with S—S bridge between Cys residues |
| 5. | Hcys—Pro—Phe—Cys—Sta—Leu—Phe—OCH$_3$ with S—S bridge between Hcys and Cys |
| 6. | Cys—Pro—Phe—Hcys—Sta—Leu—Phe—OCH$_3$ with S—S bridge between Cys and Hcys |

For the peptides prepared above, various analytical methods were carried out to verify the structure of the peptide products. The following table indicates which methods were employed and summarizes the results where practicable.

| Example No. | Analytical Method | | | | | |
|---|---|---|---|---|---|---|
| | TLC[1] | HPLC[2] | AA[3] | EA[4] | NMR[5] | FAB[6] |
| 4 | 90+% | 88% | X | X | X | X |
| 5 | 90+% | 70% | X | X | X | X |
| 6 | 95+% | —* | —* | X | —* | X |

[1] TLC = thin layer chromatography on silica gel; visualization by reagents which tend to detect peptides; % refers to estimated purity.
[2] HPLC = high pressure liquid chromatography; detection by ultraviolet absorption at 240 nm or 210 nm; chromatography is reverse phase; % refers to purity.
[3] AA = amino acid analysis; peptides are hydrolyzed to their component amino acids, which are then quantitatively measured; values should be 1.00 ± 0.03.
[4] EA = elemental analysis
[5] NMR = nuclear magnetic resonance spectroscopy at 360 MHz for protons; X = spectrum consistent with structure; — = not performed.
[6] FAB = fast atom bombardment mass spectrum; confirms molecular weight expected for monomeric cycle; X = spectrum consistent with structure; — = not performed.
*Analyses performed on N$^\alpha$-BOC precursor and found to be within acceptable limits.

EXAMPLE 7

Hog Renin Inhibition

An assay was carried out in order to determine the inhibitory potency of the peptides of the present invention. The assay measured the inhibition of hog kidney renin, and was in accordance with the procedure described in Rich et al., *J. Med. Chem.* 23:27, 1980, except that a pH of 7.3 was used. The results of the assay, illustrated in the table below, are expressed as I$_{50}$ values, which refers to the concentration of peptide inhibitor necessary to produce 50% inhibition of renin activity. This I$_{50}$ value is obtained typically by plotting data from four inhibitor concentrations. Pepstatin was used as an active control.

| Peptide | I$_{50}$ (M) |
|---|---|
| Hcys—Pro—Phe—Hcys—Sta—Leu—Phe—OCH$_3$ (S—S bridge) | 4.9 × 10$^{-8}$ |
| BOC—Hcys—Pro—Phe—Hcys—Sta—Leu—Phe—OCH$_3$ (S—S bridge) | 2.9 × 10$^{-7}$ |
| Cys—Pro—Phe—Cys—Sta—Leu—Phe—OCH$_3$ (S—S bridge) | 2.2 × 10$^{-6}$ |
| Hcys—Pro—Phe—Cys—Sta—Leu—Phe—OCH$_3$ (S—S bridge) | 2.8 × 10$^{-7}$ |
| Cys—Pro—Phe—Hcys—Sta—Leu—Phe—OCH$_3$ (S—S bridge) | 3.1 × 10$^{-6}$ |

EXAMPLE 8

Human Renin Inhibition

An assay was carried out in order to determine the inhibitory potency of the peptides of the present invention. The assay measured the inhibition of human kidney renin purified as described in Bangham, D. R., Robertson, I., Robinson, J. I. S., Robinson, C. J., and Tree, M., *Clinical Science and Molecular Medicine*, 48 (Supp. 2): 136s–159s (1975), and further purified by affinity chromatography on pepstatin-aminohexyl-Sepharose as described in Poe, M., Wu., J. K., Florance, J. R., Radkey, J. A., Bennett, C. D., and Hoogsteen, K., *J. Biol. Chem.* (1982, in press). The assay was also in accordance with Poe et al. cited above. Results are expressed as $K_I$ values, which refer to the dissociation constant of the inhibited enzyme-inhibitor complex. This $K_I$ value was obtained as described above. Pepstatin was used as an active control. The results are set out in the table below.

| Peptide | $K_I(M)$ |
|---|---|
| Hcys—Pro—Phe—Hcys—Sta—Leu—Phe—OCH$_3$ (S——S) | $4.1 \times 10^{-7}$ |

What is claimed is:

1. A peptide of the formula:

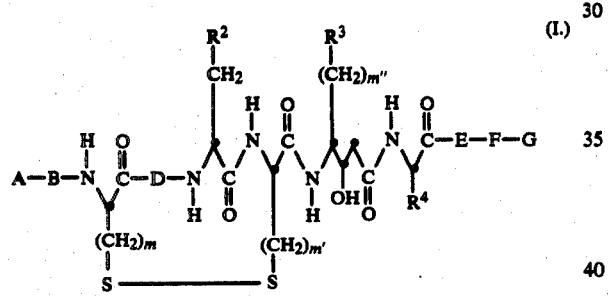

(I.)

wherein:

A is hydrogen; or

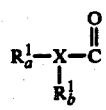

where X is

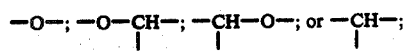

and $R_a^1$ and $R_b^1$ may be the same or different and are hydrogen; Y—(CH$_2$)$_n$—where Y is C$_{1-4}$alkyl; hydrogen; aryl; C$_{3-7}$cycloalkyl; or C$_{3-7}$cycloalkyl or aryl substituted with up to five members independently selected from the group consisting of C$_{1-8}$alkyl, trifluoromethyl, hydroxy, C$_{1-4}$alkoxy, and halo; n is 0 to 5; except that where X is —O—, only one of $R_a^1$ or $R_b^1$ is present;

B is absent; glycyl; sarcosyl; or

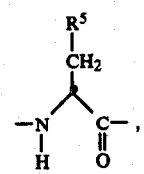

where $R^5$ is hydrogen; C$_{1-4}$ alkyl; hydroxy C$_{1-4}$ alkyl; aryl; aryl substituted with up to three members selected from the group consisting of C$_{1-4}$alkyl, trifluoromethyl, hydroxy, C$_{1-4}$alkoxy, and; halo; indolyl; 4-imidazolyl; amino C$_{2-4}$ alkyl; guanidyl C$_{2-3}$ alkyl; or methylthiomethyl;

D is

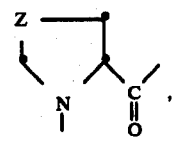

where Z is —(CH$_2$)$_p$—and p is 1 or 2; or —S—;

E is absent; or

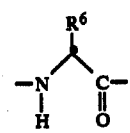

where $R^6$ is hydrogen;

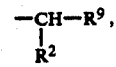

where $R^9$ is hydrogen, C$_{1-4}$alkyl, hydroxy, or C$_{3-7}$cycloalkyl; or —CH$_2$R$^{10}$, where R$^{10}$ is 4-imidazolyl, amino-C$_{2-4}$alkyl, 2-, 3- or 4-pyridyl, or guanidyl-C$_{2-3}$alkyl;

F is absent; glycyl; sarcosyl; or

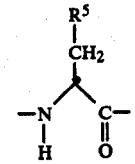

where $R^5$ is as defined above;

G is OR; NHR; N(R)$_2$, where each R may be the same or different and is hydrogen; or C$_{1-4}$alkyl; or, when E and/or F are absent, G may be (1) —Y—(CH$_2$)$_q$—R$^7$ where Y is —NH— or —O—; q is 0 to 5; and R$^7$ is hydrogen; hydroxy; C$_{1-4}$alkyl; C$_{3-7}$cycloalkyl; aryl; aryl substituted with up to five members independently selected from the group consisting of C$_{1-6}$alkyl, trifluoromethyl, hydroxy, C$_{1-4}$alkoxy, amino, mono- or diC$_{1-4}$alkylamino, and halo; amino; mono-, di- or tri-C$_{1-4}$alkylamino; guanidyl; heterocyclic; or heterocyclic substituted with up to five members independently selected from the group consisting of C$_{1-6}$alkyl, hydroxy, trifluoromethyl, C$_{1-4}$alkoxy, halo, aryl, aryl-$C_{1-4}$alkyl, amino, and mono- or di-$C_{1-4}$alkylamino;

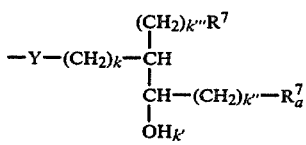 (2)

where Y is as defined above; k is 0 or 1; k' is 0 or 1; k'' is 1 to 4; k''' is 1 to 4; and $R^7$ and $R_a^7$ may be the same or different and have the same meaning as $R^7$ above and $R_a^7$ may additionally be

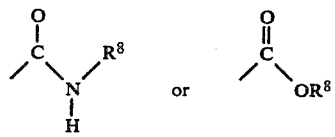

where $R^8$ is hydrogen or $C_{1-3}$alkyl; or

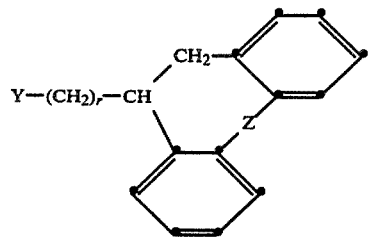 (3)

where Y is as defined above; r is 0 or 1; and Z is

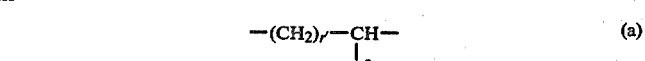 (a)

where r' is 0 or 1; and $R^8$ is a defined above; or

 (b)

where r'' is 0 or 1;

$R^2$ is hydrogen; $C_{1-4}$alkyl; aryl; aryl substituted with up to three members selected from the group consisting of $C_{1-4}$alkyl, trifluoromethyl, hydroxy, $C_{1-4}$alkoxy, and halo; or indolyl;

$R^3$ is $C_{3-6}$ alkyl; $C_{3-7}$ cycloalkyl; aryl; or $C_{3-7}$cycloalkyl or aryl substituted with up to three members selected from the group consisting of $C_{1-4}$alkyl, trifluoromethyl, hydroxy, $C_{1-4}$alkoxy, and halo;

$R^4$ is hydrogen; or

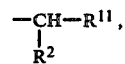

'where $R^{11}$ is hydrogen; $C_{1-4}$alkyl; hydroxy; or $C_{3-7}$cycloalkyl; and $R^2$ is as defined above; and m is 1 or 2;
m' is 1 or 2;
m'' is 1 to 4; and wherein all of the asymmetric carbon atoms have an S configuration, except for those in the A, B, D, F, and G substituents, which may have an S or R configuration; and a pharmaceutically acceptable salt thereof.

2. A peptide according to claim 1 wherein the peptide is a member selected from the group consisting essentially of:

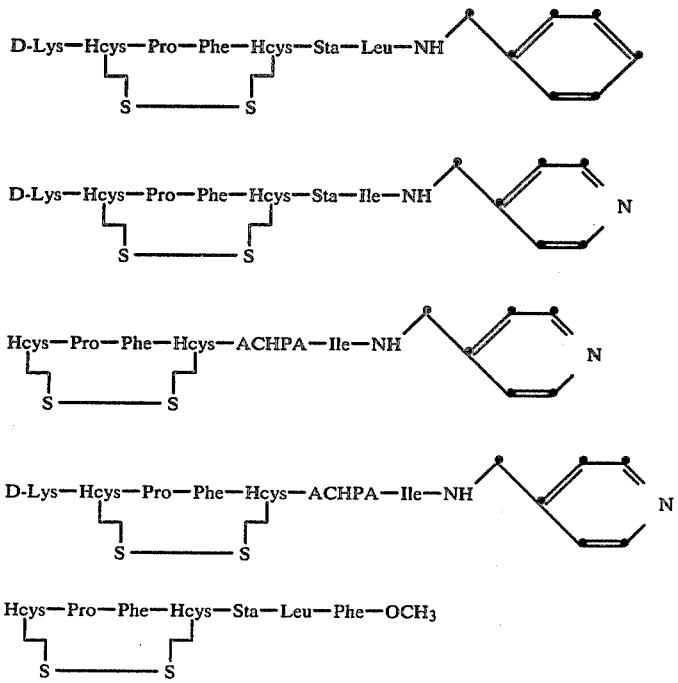

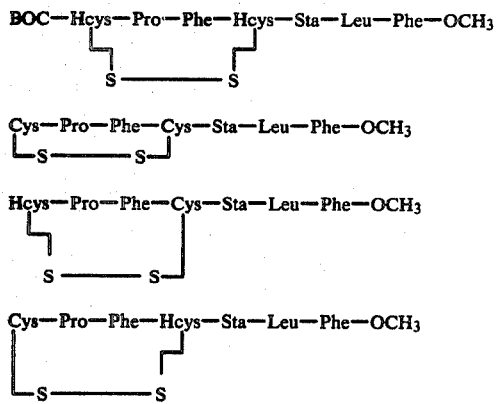

3. A pharmaceutical composition for treating renin-associated hypertension or hyperaldosteronism, comprising a pharmaceutical carrier and a therapeutically effective amount of a peptide of the formula:

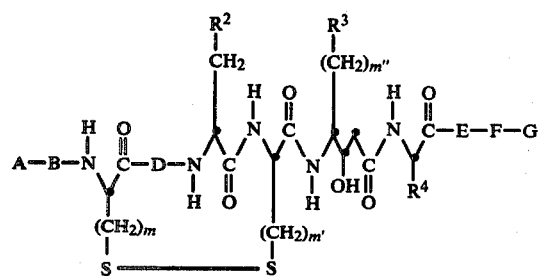

wherein:
A is hydrogen; or

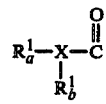

where X is

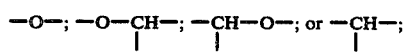

and $R_a^1$ and $R_b^1$ may be the same or different and are hydrogen; Y—$(CH_2)_n$— where Y is $C_{1-4}$alkyl; hydrogen; aryl; $C_{3-7}$cycloalkyl; or $C_{3-7}$cycloalkyl or aryl substituted with up to five members independently selected from the group consisting of $C_{1-8}$alkyl, trifluoromethyl, hydroxy, $C_{1-4}$alkoxy, and halo; n is 0 to 5; except that where X is —O—, only one of $R_a^1$ or $R_b$ is present;
B is absent; glycyl; sarcosyl; or

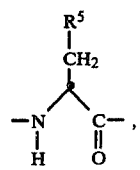

where $R^5$ is hydrogen; $C_{1-4}$ alkyl; hydroxy $C_{1-4}$ alkyl; aryl; aryl substituted with up to three members selected from the group consisting of $C_{1-4}$alkyl, trifluoromethyl, hydroxy, $C_{1-4}$alkoxy, and; halo; indolyl; 4-imidazolyl; amino $C_{2-4}$ alkyl; guanidyl $C_{2-3}$ alkyl; or methylthiomethyl;
D is

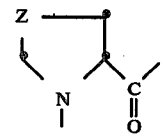

where Z is —$(CH_2)_p$— and p is 1 or 2; or —S—;
E is absent; or

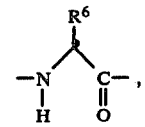

where $R^6$ is hydrogen;

$$-CH-R^9,$$
$$\phantom{-}|\phantom{-R^9,}$$
$$\phantom{-}R^2$$

where $R^9$ is hydrogen, $C_{1-4}$alkyl, hydroxy, or $C_{3-7}$cycloalkyl; or —$CH_2R^{10}$, where $R^{10}$ is 4-imidazolyl, amino-$C_{2-4}$alkyl, 2-, 3- or 4-pyridyl, or guanidyl-$C_{2-3}$alkyl;
F is absent; glycyl; sarcosyl; or

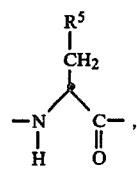

where $R^5$ is as defined above;
G is OR; NHR; N(R)$_2$, where each R may be the same or different and is hydrogen; or $C_{1-4}$alkyl; or, when E and/or F are absent, G may be (1) —Y—$(CH_2)_q$—$R^7$ where Y is —NH— or —O—; q is 0 to 5; and $R^7$ is hydrogen; hydroxy; $C_{1-4}$alkyl; $C_{3-7}$cycloalkyl; aryl; aryl substituted with up to five members independently selected from the group consisting of $C_{1-6}$alkyl, trifluoromethyl, hydroxy, $C_{1-4}$alkoxy, amino, mono- or di$C_{1-4}$alkylamino, and halo; amino; mono-, di- or tri-$C_{1-4}$alkylamino; guanidyl; heterocyclic; or heterocyclic substituted with up to five members independently selected from the group consisting of $C_{1-6}$alkyl, hydroxy, trifluoromethyl, $C_{1-4}$alkoxy, halo, aryl, aryl-$C_{1-4}$alkyl, amino, and mono- or di-$C_{1-4}$alkylamino;

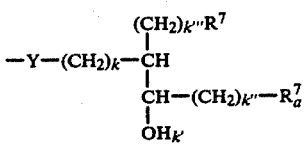 (2)

where Y is as defined above; k is 0 or 1; k' is 0 or 1; k" is 1 to 4; k''' is 1 to 4; and $R^7$ and $R_a^7$ may be the same or different and have the same meaning as $R^7$ above and $R_a^7$ may additionally be

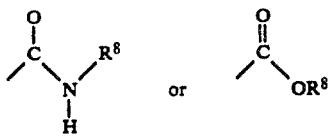

where $R^8$ is hydrogen or $C_{1-3}$alkyl; or

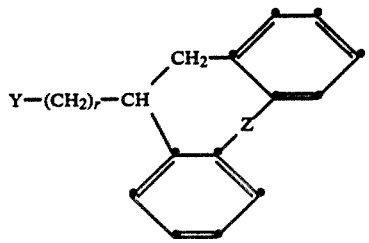 (3)

where Y is as defined above; r is 0 or 1; and Z is

 (a)

where r' is 0 or 1; and $R^8$ is as defined above; or

 (b)

where r" is 0 or 1;

$R^2$ is hydrogen; $C_{1-4}$alkyl; aryl; aryl substituted with up to three members selected from the group consisting of $C_{1-4}$alkyl, trifluoromethyl, hydroxy, $C_{1-4}$alkoxy, and halo; or indolyl;

$R^3$ is $C_{3-6}$ alkyl; $C_{3-7}$ cycloalkyl; aryl; or $C_{3-7}$cycloalkyl or aryl substituted with up to three members selected from the group consisting of $C_{1-4}$alkyl, trifluoromethyl, hydroxy, $C_{1-4}$alkoxy, and halo;

$R^4$ is hydrogen; or $$-\underset{\underset{R^2}{|}}{CH}-R^{11},$$

where $R^{11}$ is hydrogen; $C_{1-4}$alkyl; hydroxy; or $C_{3-7}$cycloalkyl; and $R^2$ is as defined above; and m is 1 or 2;
m' is 1 or 2;
m" is 1 to 4; and wherein all of the asymmetric carbon atoms have an S configuration, except for those in the A, B, D, F, and G substituents, which may have an S or R configuration; and a pharmaceutically acceptable salt thereof.

4. A composition according to claim 3 wherein the peptide is a member selected from the group consisting essentially of:

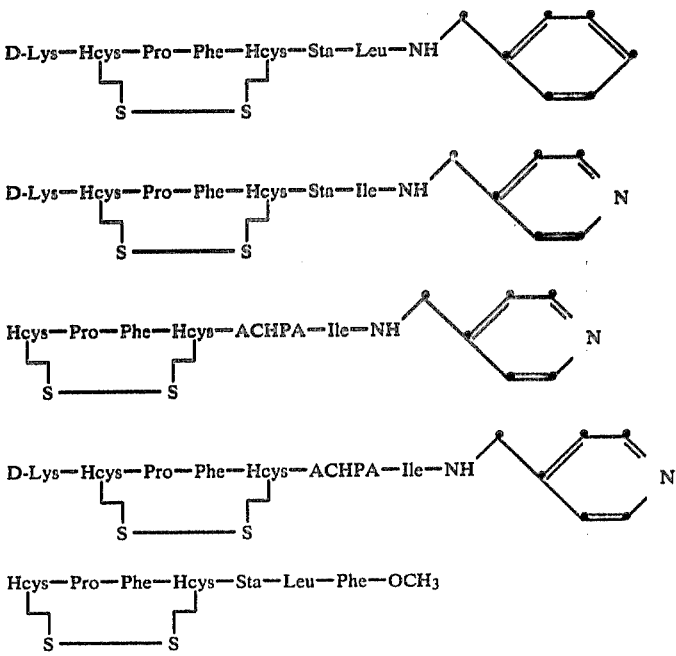

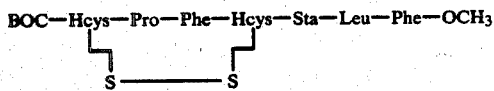

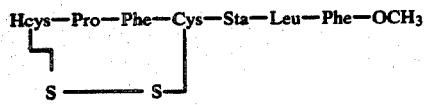

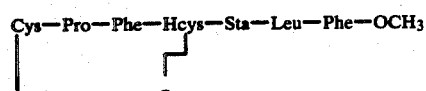

5. A method of treating renin-associated hypertension comprising administering to a patient in need of such treatment, a therapeutically effective amount of a peptide of the formula:

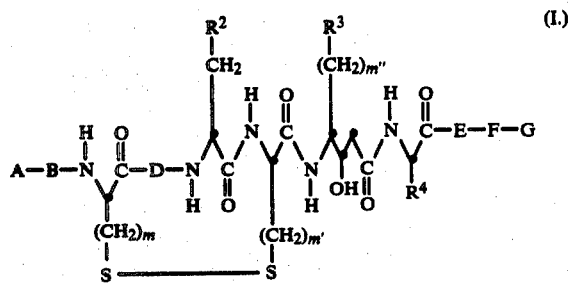 (I.)

wherein:
A is hydrogen; or

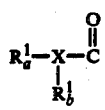

where X is

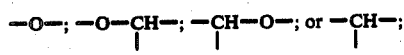

and $R_a^1$ and $R_b^1$ may be the same or different and are hydrogen; Y—(CH$_2$)$_n$— where Y is C$_{1-4}$alkyl; hydrogen; aryl; C$_{3-7}$cycloalkyl; or C$_{3-7}$cycloalkyl or aryl substituted with up to five members independently selected from the group consisting of C$_{1-8}$alkyl, trifluoromethyl, hydroxy, C$_{1-4}$alkoxy, and halo; n is 0 to 5; except that where X is —O—, only one of $R_a^1$ or $R_b^1$ is present;
B is absent; glycyl; sarcosyl; or

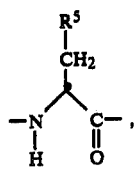

where $R^5$ is hydrogen; C$_{1-4}$ alkyl; hydroxy C$_{1-4}$ alkyl; aryl; aryl substituted with up to three members selected from the group consisting of C$_{1-4}$alkyl, trifluoromethyl, hydroxy, C$_{1-4}$alkoxy, and; halo; indolyl; 4-imidazolyl; amino C$_{2-4}$ alkyl; guanidyl C$_{2-3}$ alkyl; or methylthiomethyl;
D is

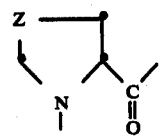

where Z is —(CH$_2$)$_p$— and p is 1 or 2; or —S—;
E is absent; or

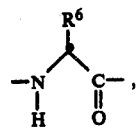

where $R^6$ is hydrogen;

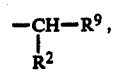

where $R^9$ is hydrogen, C$_{1-4}$alkyl, hydroxy, or C$_{3-7}$cycloalkyl; or —CH$_2$R$^{10}$, where R$^{10}$ is 4-imidazolyl, amino-C$_{2-4}$alkyl, 2-, 3- or 4-pyridyl, or guanidyl-C$_{2-3}$alkyl;
F is absent; glycyl; sarcosyl; or

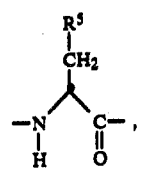

where $R^5$ is as defined above;
G is OR; NHR; N(R)$_2$, where each R may be the same or different and is hydrogen; or C$_{1-4}$alkyl; or, when E and/or F are absent, G may be (1) —Y—(CH$_2$)$_q$—R$^7$ where Y is —NH— or —O—; q is 0 to 5; and R$^7$ is hydrogen; hydroxy; $C_{1-4}$alkyl; $C_{3-7}$cycloalkyl; aryl; aryl substituted with up to five members independently selected from the group consisting of $C_{1-6}$alkyl, trifluoromethyl, hydroxy, $C_{1-4}$alkoxy, amino, mono- or di$C_{1-4}$alkylamino, and halo; amino; mono-, di- or tri-$C_{1-4}$alkylamino; guanidyl; heterocyclic; or heterocyclic substituted with up to five members independently selected from the group consisting of $C_{1-6}$alkyl, hydroxy, trifluoromethyl, $C_{1-4}$alkoxy, halo, aryl, aryl-$C_{1-4}$alkyl, amino, and mono- or di-$C_{1-4}$alkylamino;

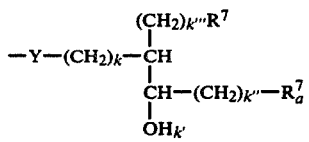
(2)

where Y is as defined above; k is 0 or 1; k' is 0 or 1; k'' is 1 to 4; k''' is 1 to 4; and $R^7$ and $R_a^7$ may be the same or different and have the same meaning as $R^7$ above and $R_a^7$ may additionally be

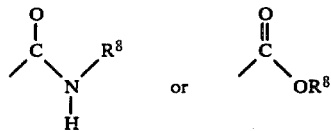

where $R^8$ is hydrogen or $C_{1-3}$alkyl; or

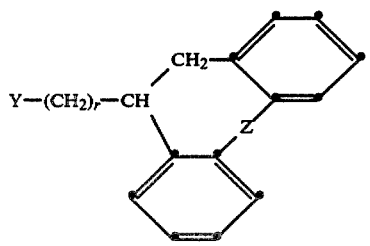
(3)

where Y is as defined above; r is 0 or 1; and Z is

(a)

where r' is 0 or 1; and $R^8$ is as defined above; or

(b)

where r'' is 0 or 1;
$R^2$ is hydrogen; $C_{1-4}$alkyl; aryl; aryl substituted with up to three members selected from the group consisting of $C_{1-4}$alkyl, trifluoromethyl, hydroxy, $C_{1-4}$alkoxy, and halo; or indolyl;
$R^3$ is $C_{3-6}$ alkyl; $C_{3-7}$ cycloalkyl; aryl; or $C_{3-7}$cycloalkyl or aryl substituted with up to three members selected from the group consisting of $C_{1-4}$alkyl, trifluoromethyl, hydroxy, $C_{1-4}$alkoxy, and halo;
$R^4$ is hydrogen; or

where $R^{11}$ is hydrogen; $C_{1-4}$alkyl; hydroxy; or $C_{3-7}$cycloalkyl; and $R^2$ is as defined above; and
m is 1 or 2;
m' is 1 or 2;
m'' is 1 to 4; and
wherein all of the asymmetric carbon atoms have an S configuration, except for those in the A, B, D, F, and G substituents, which may have an S or R configuration; and a pharmaceutically acceptable salt thereof.

6. A method according to claim 5 wherein the peptide is a member selected from the group consisting essentially of:

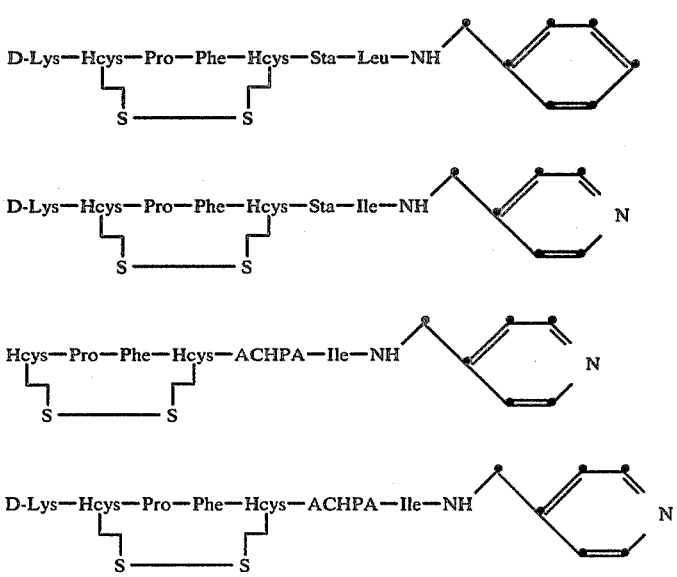

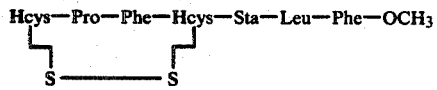

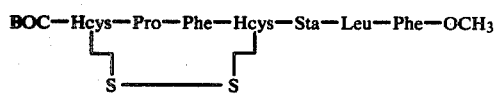

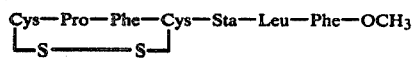

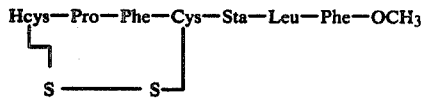

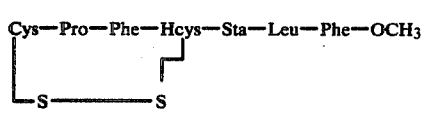

7. A method of treating renin-associated hyperaldosteronism, comprising administering to a patient in need of such treatment, a therapeutically effective amount of a peptide of the formula:

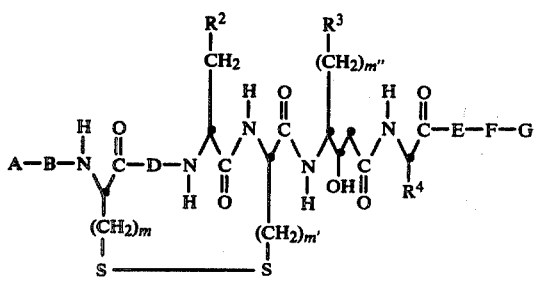

wherein:

A is hydrogen; or

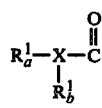

where X is

—O—; —O—CH—; —CH—O—; or —CH—;

and $R_a^1$ and $R_b^1$ may be the same or different and are hydrogen; Y—$(CH_2)_n$— where Y is $C_{1-4}$alkyl; hydrogen; aryl; $C_{3-7}$cycloalkyl; or $C_{3-7}$cycloalkyl or aryl substituted with up to five members independently selected from the group consisting of $C_{1-8}$alkyl, trifluoromethyl, hydroxy, $C_{1-4}$alkoxy, and halo; n is 0 to 5; except that where X is —O—, only one of $R_a^1$ and $R_b^1$ is present;

B is absent; glycyl; sarcosyl; or

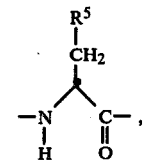

where $R^5$ is hydrogen; $C_{1-4}$ alkyl; hydroxy $C_{1-4}$ alkyl; aryl; aryl substituted with up to three member selected from the group consisting of $C_{1-4}$alkyl, trifluoromethyl, hydroxy, $C_{1-4}$alkoxy, and; halo; indolyl; 4-imidazolyl; amino $C_{2-4}$ alkyl; guanidyl $C_{2-3}$ alkyl; or methylthiomethyl;

D is

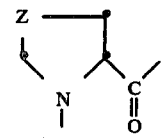

where Z is —$(CH_2)_p$— and p is 1 or 2; or —S—;

E is absent; or

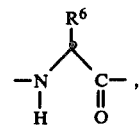

where $R^6$ is hydrogen;

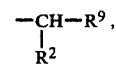

where $R^9$ is hydrogen, $C_{1-4}$alkyl, hydroxy, or $C_{3-7}$cycloalkyl; or —$CH_2R^{10}$, where $R^{10}$ is 4-imidazolyl, amino-$C_{2-4}$alkyl, 2-, 3- or 4-pyridyl, or guanidyl-$C_{2-3}$alkyl;

F is absent; glycyl; sarcosyl; or

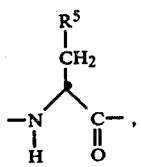

where R⁵ is as defined above;

G is OR; NHR; N(R)₂, where each R may be the same or different and is hydrogen; or C₁₋₄alkyl; or, when E and/or F are absent, G may be (1) —Y—(CH₂)$_q$—R⁷ where Y is —NH— or —O—; q is 0 to 5; and R⁷ is hydrogen; hydroxy; C₁₋₄alkyl; C₃₋₇cycloalkyl; aryl; aryl substituted with up to five members independently selected from the group consisting of C₁₋₆alkyl, trifluoromethyl, hydroxy, C₁₋₄alkoxy, amino, mono- or diC₁₋₄alkylamino, and halo; amino; mono-, di- or tri-C₁₋₄alkylamino; guanidyl; heterocyclic; or heterocyclic substituted with up to five members independently selected from the group consisting of C₁₋₆alkyl, hydroxy, trifluoromethyl, C₁₋₄alkoxy, halo, aryl, aryl-C₁₋₄alkyl, amino, and mono- or di-C₁₋₄alkylamino;

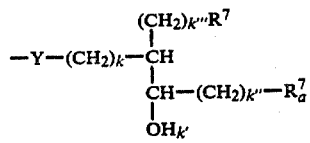 (2)

where Y is as defined above; k is 0 or 1; k' is 0 or 1; k" is 1 to 4; k'" is 1 to 4; and R⁷ and R$_a$⁷ may be the same or different and have the same meaning as R⁷ above and R$_a$⁷ may additionally be

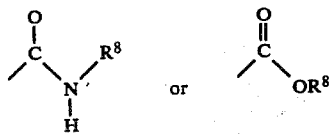

where R⁸ is hydrogen or C₁₋₃alkyl; or

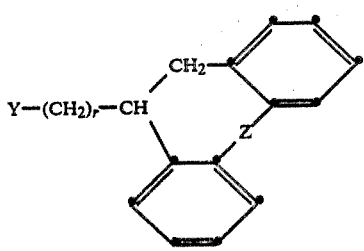 (3)

where Y is as defined above; r is 0 or 1; and Z is

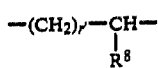 (a)

where r' is 0 or 1; and R⁸ is as defined above; or

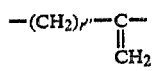 (b)

where r" is 0 or 1;

R² is hydrogen; C₁₋₄alkyl; aryl; aryl substituted with up to three members selected from the group consisting of C₁₋₄alkyl, trifluoromethyl, hydroxy, C₁₋₄alkoxy, and halo; or indolyl;

R³ is C₃₋₆ alkyl; C₃₋₇ cycloalkyl; aryl; or C₃₋₇cycloalkyl or aryl substituted with up to three members selected from the group consisting of C₁₋₄alkyl, trifluoromethyl, hydroxy, C₁₋₄alkoxy, and halo;

R⁴ is hydrogen; or

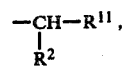

where R¹¹ is hydrogen; C₁₋₄alkyl; hydroxy; or C₃₋₇cycloalkyl; and R² is as defined above; and m is 1 or 2;

m' is 1 or 2;

m" is 1 to 4; and wherein all of the asymmetric carbon atoms have an S configuration, except for those in the A, B, D, F, and G substituents, which may have an S or R configuration; and a pharmaceutically acceptable salt thereof.

8. A method of determining the presence of renin-associated hypertension in a patient, comprising administering to such a patient, at a hypotensive dosage level as a single dose, a peptide of the formula:

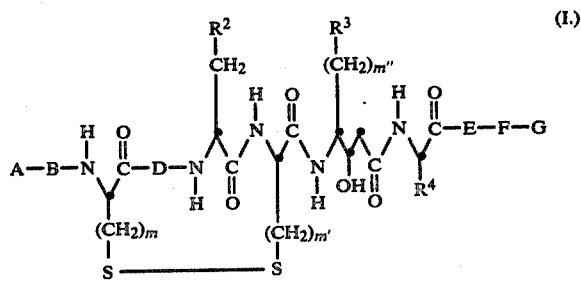 (I.)

wherein:

A is hydrogen; or

where X₁ is

and R$_a$¹ and R$_b$¹ may be the same or different and are hydrogen; Y—(CH₂)$_n$— where Y is C₁₋₄alkyl; hydrogen; aryl; C₃₋₇cycloalkyl; or C₃₋₇cycloalkyl or aryl substituted with up to five members independently selected from the group consisting of C₁₋₈alkyl, trifluoromethyl, hydroxy, C₁₋₄alkoxy, and halo; n is 0 to 5; except that where X is —O—, only one of R$_a$¹ or R$_b$¹ is present;

B is absent; glycyl; sarcosyl; or

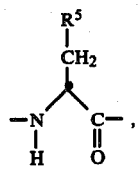

where R⁵ is hydrogen; C₁₋₄ alkyl; hydroxy C₁₋₄ alkyl; aryl; aryl substituted with up to three member selected from the group consisting of C₁₋₄alkyl, trifluoromethyl, hydroxy, C₁₋₄alkoxy, and; halo; indolyl; 4-imidazolyl; amino C₂₋₄ alkyl; guanidyl C₂₋₃ alkyl; or methylthiomethyl;

D is

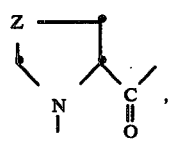

where Z is —(CH₂)$_p$— and p is 1 or 2; or —S—;
E is absent; or

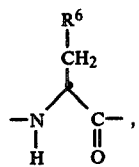

where R⁶ is hydrogen;

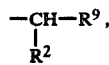

where R⁹ is hydrogen, C₁₋₄alkyl, hydroxy, or C₃₋₇cycloalkyl; or —CH₂R¹⁰, where R¹⁰ is 4-imidazolyl, amino-C₂₋₄alkyl, 2-, 3- or 4-pyridyl, or guanidyl-C₂₋₃alkyl;

F is absent; glycyl; sarcosyl; or

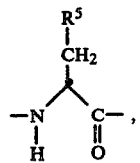

where R⁵ is as defined above;
G is OR; NHR; N(R)₂, where each R may be the same or different and is hydrogen; or C₁₋₄alkyl; or, when E and/or F are absent, G may be (1) —Y—(CH₂)$_q$—R⁷ where Y is —NH— or —O—; q is 0 to 5; and R⁷ is hydrogen; hydroxy; C₁₋₄alkyl; C₃₋₇cycloalkyl; aryl; aryl substituted with up to five members independently selected from the group consisting of C₁₋₆alkyl, trifluoromethyl, hydroxy, C₁₋₄alkoxy, amino, mono- or diC₁₋₄alkylamino, and halo; amino; mono-, di- or tri-C₁₋₄alkylamino; guanidyl; heterocyclic; or heterocyclic substituted with up to five members independently selected from the group consisting of C₁₋₆alkyl, hydroxy, trifluoromethyl, C₁₋₄alkoxy, halo, aryl, aryl-C₁₋₄alkyl, amino, and mono- or di-C₁₋₄alkylamino;

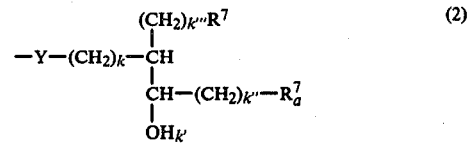

where Y is as defined above; k is 0 or 1; k' is 0 or 1; k" is 1 to 4; k''' is 1 to 4; and R⁷ and R$_a$⁷ may be the same or different and have the same meaning as R⁷ above and R$_a$⁷ may additionally be

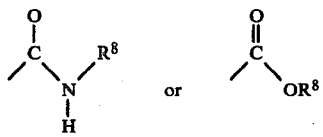

where R⁸ is hydrogen or C₁₋₃alkyl; or

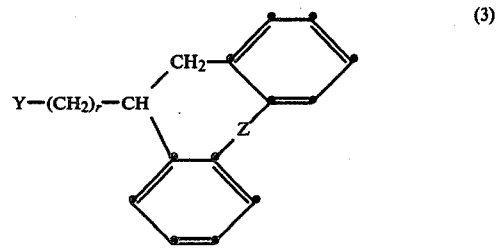

where Y is as defined above; r is 0 or 1; and Z is

where r' is 0 or 1; and R⁸ is as defined above; or

where r" is 0 or 1;
R² is hydrogen; C₁₋₄alkyl; aryl; aryl substituted with up to three members selected from the group consisting of C₁₋₄alkyl, trifluoromethyl, hydroxy, C₁₋₄alkoxy, and halo; or indolyl;
R³ is C₃₋₆ alkyl; C₃₋₇ cycloalkyl; aryl; or C₃₋₇cycloalkyl or aryl substituted with up to three members selected from the group consisting of C₁₋₄alkyl, trifluoromethyl, hydroxy, C₁₋₄alkoxy, and halo;
R⁴ is hydrogen; or

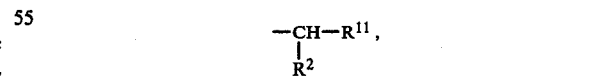

where R¹¹ is hydrogen; C₁₋₄alkyl; hydroxy; or C₃₋₇cycloalkyl; and R² is as defined above; and
m is 1 or 2;
m' is 1 or 2;
m" is 1 to 4; and
wherein all of the asymmetric carbon atoms have an S configuration, except for those in the A, B, D, F, and G substituents, which may have an S or R configuration; and a pharmaceutically acceptable salt thereof; followed by monitoring of said patient's blood pressure.

* * * * *